(12) United States Patent
Hermel-Davidock et al.

(10) Patent No.: US 10,654,979 B2
(45) Date of Patent: May 19, 2020

(54) AMPHIPHILIC GRAFT COPOLYMERS

(71) Applicant: Becton, Dickinson and Company, Franklin Lakes, NJ (US)

(72) Inventors: Theresa Hermel-Davidock, Vernon Hills, IL (US); Jianbin Zhang, Livingston, NJ (US); Tea Datashvili, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 45 days.

(21) Appl. No.: 16/058,366

(22) Filed: Aug. 8, 2018

(65) Prior Publication Data

US 2019/0055366 A1 Feb. 21, 2019

Related U.S. Application Data

(60) Provisional application No. 62/547,169, filed on Aug. 18, 2017.

(51) Int. Cl.
| | | |
|---|---|---|
| *C08G 81/02* | (2006.01) | |
| *C08L 23/12* | (2006.01) | |
| *C08L 23/14* | (2006.01) | |
| *A61M 5/14* | (2006.01) | |
| *C08L 23/10* | (2006.01) | |
| *A61L 29/04* | (2006.01) | |
| *A61L 29/06* | (2006.01) | |
| *A61M 25/00* | (2006.01) | |
| *A61M 39/10* | (2006.01) | |

(52) U.S. Cl.
CPC .......... *C08G 81/025* (2013.01); *A61L 29/041* (2013.01); *A61L 29/049* (2013.01); *A61L 29/06* (2013.01); *C08L 23/10* (2013.01); *C08L 23/12* (2013.01); *C08L 23/142* (2013.01); *A61M 5/14* (2013.01); *A61M 25/00* (2013.01); *A61M 39/10* (2013.01); *A61M 2205/02* (2013.01); *A61M 2207/00* (2013.01); *C08L 2203/02* (2013.01)

(58) Field of Classification Search
CPC .................................................. C08G 81/025
See application file for complete search history.

(56) References Cited

U.S. PATENT DOCUMENTS

| 4,269,788 A | 3/1981 | Muller et al. |
| 4,727,120 A | 2/1988 | Nogues |
| 5,214,091 A | 5/1993 | Tanaka et al. |
| (Continued) | | |

FOREIGN PATENT DOCUMENTS

| CN | 101055422 A | 10/2007 |
| EP | 0422804 A2 | 4/1991 |
| (Continued) | | |

OTHER PUBLICATIONS

"PCT International Search Report and Written Opinion in PCT/US2013/056176, dated Jun. 4, 2014", 12 pages.
(Continued)

*Primary Examiner* — Jeffrey C Mullis
(74) *Attorney, Agent, or Firm* — Servilla Whitney LLC

(57) ABSTRACT

Amphiphilic graft copolymers comprise a polypropylene backbone and polyoxyalkylene side-chains (PPMA-g-PEO-PPO). These copolymers are suitable as additives to base polymeric formulations for medical devices for improving bond strength, paintability, dyeability, and printablity.

6 Claims, 7 Drawing Sheets

(56) References Cited

U.S. PATENT DOCUMENTS

| | | | |
|---|---|---|---|
| 5,292,803 | A | 3/1994 | Ohmae et al. |
| 5,424,150 | A | 6/1995 | Ohnishi et al. |
| 5,721,315 | A | 2/1998 | Evans et al. |
| 5,705,603 | A | 6/1998 | Krull et al. |
| 5,948,839 | A * | 9/1999 | Chatterjee ............... C08L 23/12 524/108 |
| 6,306,964 | B1 * | 10/2001 | Evans ....................... C08F 8/30 525/74 |
| 6,433,080 | B1 | 8/2002 | Fujiki et al. |
| 6,774,181 | B1 | 8/2004 | Bechara et al. |
| 9,150,674 | B2 | 10/2015 | Hermel-Davidock et al. |
| 9,703,108 | B2 | 7/2017 | Simon et al. |
| 2008/0273820 | A1 | 11/2008 | Wiker et al. |
| 2010/0111167 | A1 | 5/2010 | Wu et al. |
| 2011/0021602 | A1 * | 1/2011 | Devore .................. A61K 31/70 514/44 A |
| 2013/0172220 | A1 | 7/2013 | Rune, Jr. |
| 2014/0058045 | A1 | 2/2014 | Hermel-Davidock et al. |

FOREIGN PATENT DOCUMENTS

| | | |
|---|---|---|
| JP | 50-112494 A | 9/1975 |
| JP | 5232796 B2 | 7/2013 |
| WO | 9627622 A1 | 9/1996 |
| WO | 9703108 A1 | 1/1997 |
| WO | 0012801 A1 | 3/2000 |

OTHER PUBLICATIONS

"PCT International Search Report and Written Opinion in PCT/US2018/046873, dated Dec. 7, 2018", 11 pages.

Chen, et al., ""Break Through in Breathable Polymers: Morphology, Properties, and Performance"", Dupont, Wilmington, DE, 1-8.

Gugliuzza, et al., ""Role of additives in the water vapor transport through block co-poly(amide/ether) membranes: effects on surface and bulk polymer properties"", European Polymer Journal 40, 2004, 2381-2389.

Jonquieres, Anne, et al., "Permeability of block copolymers to vapors and liquids", Prog. Polym. Sci. 27, 2002, 1803-1877.

Metz, S. J., et al., "Gas-Permeation Properties of Poly(ethylene oxide) Poly(butylene terephthalate) Block Copolymers", Macromolecules 37, 2004, 4590-4597.

Metz, S. J., et al., "Water vapor and gas transport through a poly(butylene terephthalate) poly(ethylene oxide) block copolymer", Desalination 148, 2002, 303-307.

Mueller, Chad, et al., "Breathable Polymer Films Produced by the Microlayer Coextrusion Process", Journal of Applied Polymer Science, vol. 78, 2000, 816-828.

Nandi, Souvik, et al., "Open-pore morphology of i-PP copolymer crystallized from a gel state in supercritical propane", Polymer 45, 2004, 4819-4827.

Peddada, Lavanya Y., et al., "Novel graft copolymers enhance in vitro delivery of antisense oligonucleotides in the presence of serum", NIH Public Access, Dec. 3, 2009, 1-19.

Sirkar, Kamalesh K., "Membranes, Phase Interfaces, and Separations: Novel Techniques and Membranes—An Overview", Ind. Eng. Chem. Res. 47, 2008, 5250-5266.

Winter, H. Henning, et al., "Rigid Pore Structure from Highly Swollen Polymer Gels", Macromolecules 35, 2002, 3325-3327.

* cited by examiner

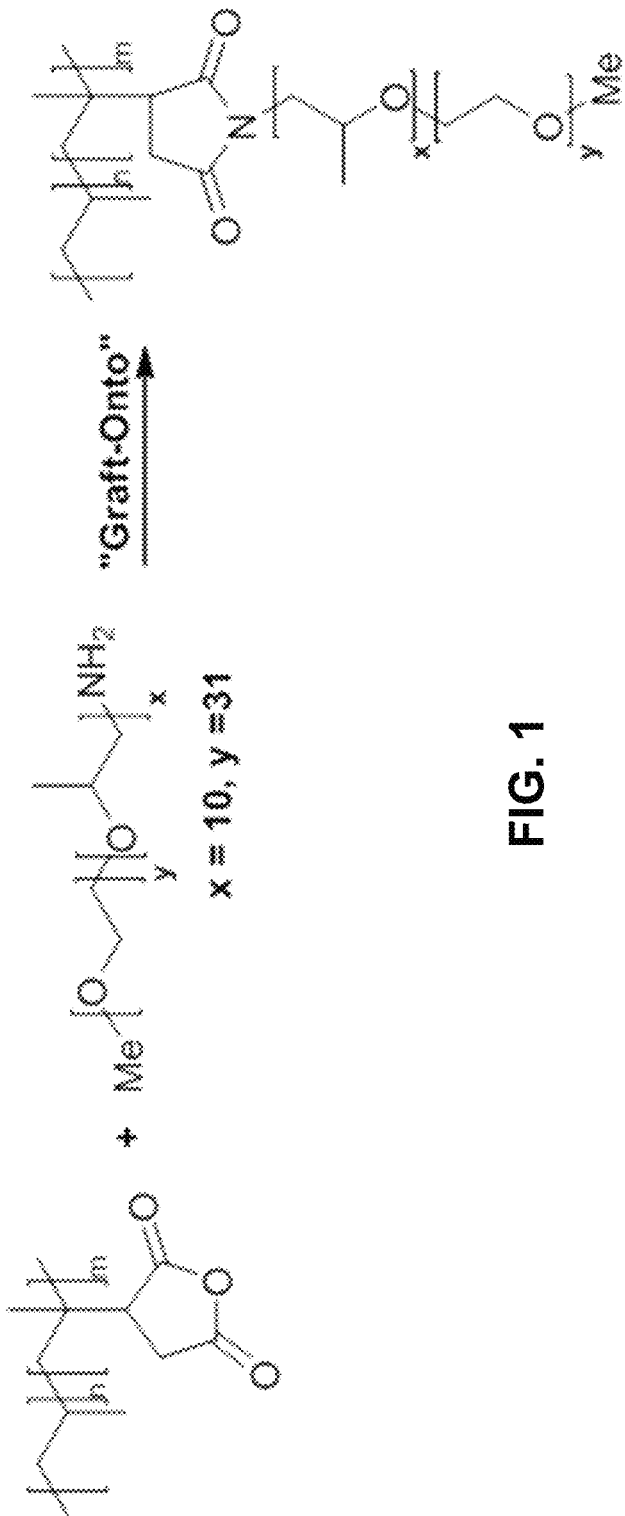
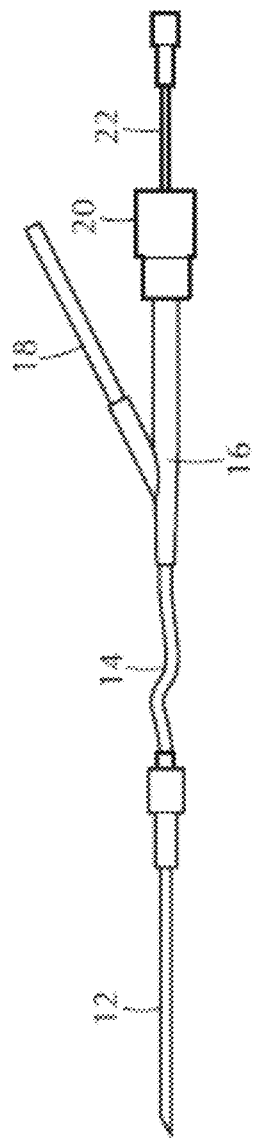
FIG. 1
FIG. 2

AMPHIPHILIC GRAFT COPOLYMERS

CROSS-REFERENCE TO RELATED APPLICATIONS

This application claims priority under 35 U.S.C. § 119(e) to U.S. Provisional Application No. 62/547,169, filed Aug. 18, 2017, the disclosure of which is incorporated herein by reference in its entirety.

TECHNICAL FIELD

Principles and embodiments of the present invention relate generally to amphiphilic graft copolymers. Functionalized polypropylene copolymers are disclosed. Specifically, polypropylene-based graft copolymers are prepared from maleated polypropylene (PP-g-MA), which is functionalized with a polymeramine, namely a polyoxyalkylene amine. The polypropylene-based graft copolymers have a polypropylene backbone and polyoxyalkylene side-chains connected with an imide linkage (PPMA-g-PEO-PPO).

BACKGROUND

Medical devices, for example tubing, are commonly made from polyolefin (e.g., ethylene- or propylene-containing) or thermoplastic elastomer (TPE) materials. Functional properties can be incorporated into known polymers to provide desired traits. U.S. Pat. No. 9,150,674 is directed to amphiphilic graft copolymers involving grafting either poly(ethylene oxide) or polylactide side chains onto known polymers, such as poly(ethylene-co-vinyl acetate) or maleic anhydride-grafted polypropylene.

Maleic anhydride-grafted polyolefins, also referred to as maleated polyolefins, may be used as an additive as a coupling agent for polymer composites. Because of its polarity and anhydride functionality, it may be used for laminating, or as a compatibilizer for polyolefin blends with nylon or EVOH, and for enhancing the strength of composites that utilize reinforcements/fillers such as glass, talc, calcium carbonate, and metals.

Polymeramines have been used primarily in polyurethane, polyureas, and thermo-plastic polyamide coating technologies, adhesives, epoxy applications and pigment formulations to increase flexibility, toughness, hydrophilicity or hydrophobicity (depending on the product used).

There are commercial products of acid and anhydride functionalized polyolefin, but there are few polar composites that are capable of effectively reacting and/or coupling with same. It is a challenge to functionalize PP due to a difficulty to control final structure and very often modification results in degradation of PP.

WO1996027622 discloses a method of producing nucleophilic amine functionalized polyolefins by reacting a polymer carrying an electrophilic functional group with a diamine having amino end-groups with different reactivity.

There is a continuing need to improve bond strength of medical devices along with their paintability, dyeability, and printablity.

SUMMARY

Provided are amphiphilic graft copolymers based on polypropylene backbone and polyoxyalkylene side-chains. They are functionalized polypropylene copolymers. The graft copolymers may be co-blended with base formulations to enhance properties of medical devices that are formed by injection molding or by extrusion.

In a first aspect, provided is an amphiphilic copolymer of Formula (I):

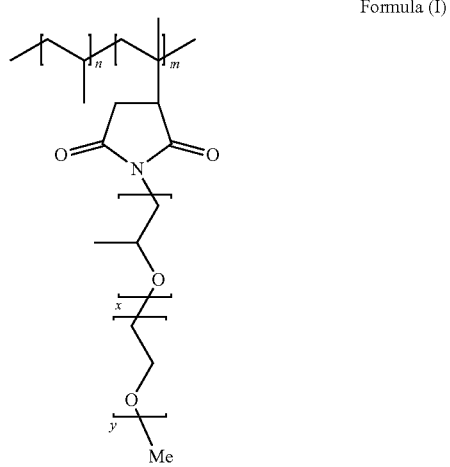

Formula (I)

wherein Me is $CH_3$; the molar value of m is in the range from 5 to 25 mole percent; and the molar value of n is in the range from 75 to 95 mole percent; the molar value of x is in the range from >0 to 40 propylene oxide units; and the molar value of y is in the range from >0 to 80 ethylene oxide units.

The amphiphilic copolymer may have a weight average molecular weight (Mw) in the range of about 5,000 to about 300,000 g/mol. The amphiphilic copolymer may have a molar ratio of EO:PO of 2:1 or greater. The amphiphilic copolymer may having a dispersity index in the range of 1.5 to 9.

In another aspect, a process for preparing an amphiphilic copolymer comprises: obtaining a maleated polypropylene; and polymerizing the maleated polypropylene with a polymeramine having monoamine functionality to form the amphiphilic copolymer; wherein the amphiphilic copolymer comprises a polypropylene backbone and polyoxyalkylene side-chains. The amphiphilic copolymer is according to Formula (I) in one or more embodiments.

The polymerization may be performed at a reaction temperature in the range of 120° C. to 240° C. The polymerization may be performed via solution polymerization. The polymerization may be performed via melt processing.

A further aspect is a medical device formed from a blend comprising: a base polymeric formulation comprising at least a polymer or co-polymer of propylene; and an additive comprising a polypropylene-poly(ethylene oxide)-poly(propylene oxide) amphiphilic graft copolymer (PPMA-g-PEO-PPO); the PPMA-g-PEO-PPO being present in the blend in an amount in the range of about 0.01 to about 5.0% by weight of the blend. The PPMA-g-PEO-PPO is according to Formula (I) in one or more embodiments. The base polymeric formulation may comprise polypropylene, a polyethylene-polypropylene co-polymer, a polypropylene-containing thermoplastic elastomer (TPE), or combinations thereof. The PPMA-g-PEO-PPO may be a product of polymerization of a maleated polypropylene and a polymeramine having monoamine functionality. The PPMA-g-PEO-PPO may have a weight average molecular weight (Mw) in the range of about 5,000 to about 300,000 g/mol. The PPMA-g-PEO-PPO may have a molar ratio of EO:PO of 2:1 or greater. The PPMA-g-PEO-PPO may have a dispersity index in the range of 1.5 to 9. The medical device may be in the form of tubing.

BRIEF DESCRIPTION OF THE DRAWINGS

FIG. 1 is a synthetic scheme for the preparation amphiphilic graft copolymers formed from maleated polypropylene (PP-g-MA) and a polyoxyalkylene amine to form a functionalized polypropylene (PPMA-g-PEO-PPO);

FIG. 2 is a plan view illustrating a portion of an exemplary intravenous (IV) infusion kit comprising tubing, an IV injection port, and connection;

DETAILED DESCRIPTION

Figure 3:
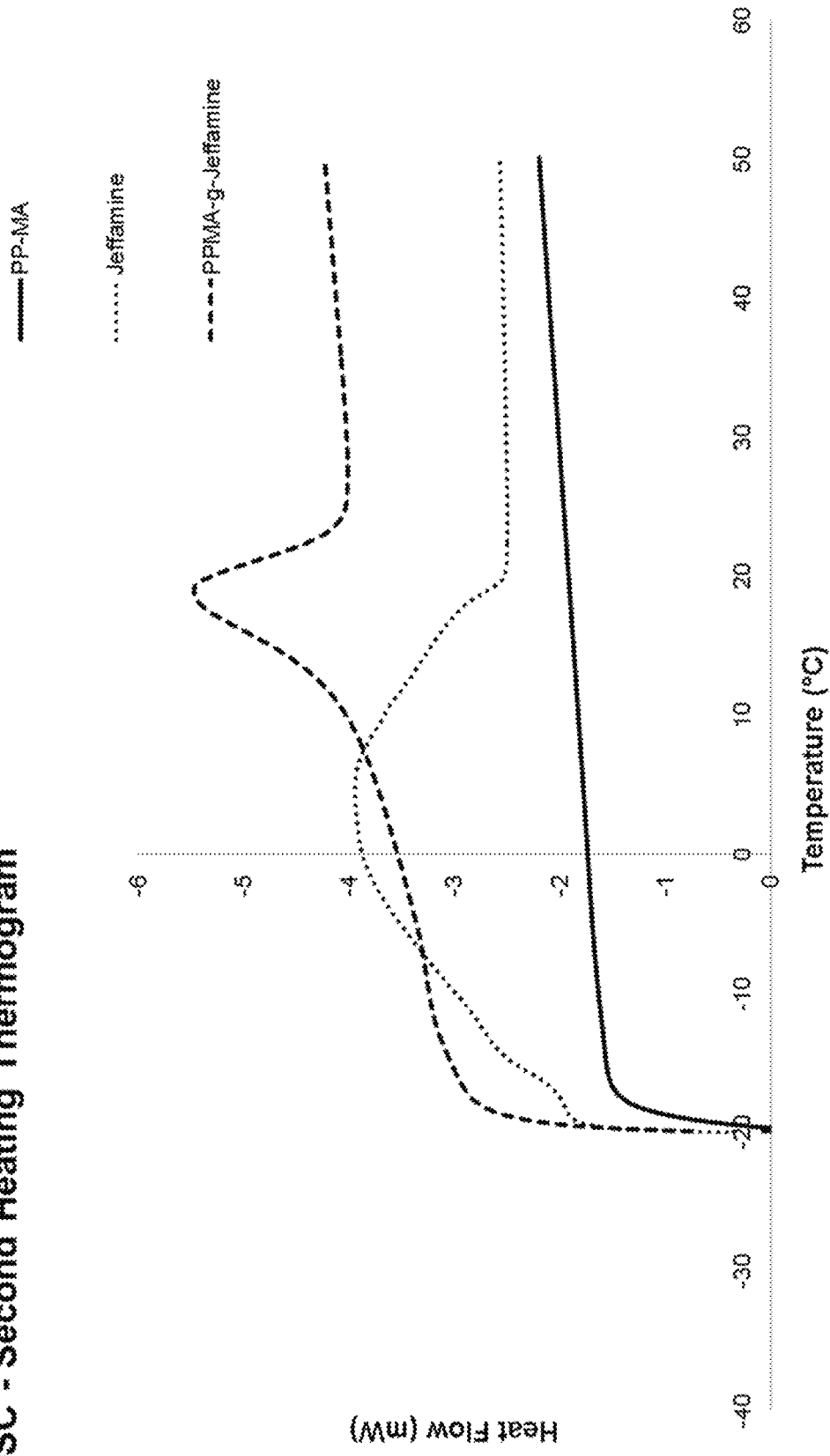
FIG. 3 is a thermogram of heat flow (mW) for the starting materials and final polymer versus temperature (° C.) for a first range of temperatures during a second heating.

Before describing several exemplary embodiments of the invention, it is to be understood that the invention is not limited to the details of construction or process steps set forth in the following description. The invention is capable of other embodiments and of being practiced or being carried out in various ways.

Amphiphilic graft copolymers disclosed herein are functionalized-polypropylene (PP) materials, which are formed from grafting-onto functionalization methodology of a maleated PP resin based on a primary amine reaction with an anhydride to form an imide. The grafting of amine-terminated polymers to maleated PP (PP-g-MA) promotes attachment of polar groups to polypropylene in accordance with FIG. 1 to form PPMA-g-PEO-PPO. Modification reaction may be done either by reactive blending in the extruder or through reaction in a suitable solvent. Functionalized-PP materials improve interaction/adhesion of the functionalized polymer with other polar surfaces. The amphiphilic graft copolymers of the present disclosure can be used to enhance base polymer formulations to improve their properties with respect to, for example, blending, bonding, paintability, dyeability, printability. Moreover, due to formation of long chain branches, functionalized-PP materials also demonstrate improved processability and mechanical properties relative to commercial PP with no functionalization, which can lack desirable rheological properties. Commercial PP usually exhibits relatively low melt strength, leading to the absence of general PP materials in thermoforming, extrusion coating and blow molding. Functionalized-PP materials can be utilized in the applications where conventional PP cannot be used, for example PP foam applications.

Principles and embodiments of the present invention relate to chemical modification of commodity polyolefins via a chemical grafting-approach to develop amphiphilic copolymers. Maleated polyolefins are one such commodity polyolefin used as a coupling agent for polymer composites. Polymeramines offer various reactivities, good temperature stabilities, are essentially colorless, and have a low viscosity. Polymeramines contain primary amino groups attached to the end of a polymer backbone normally based on propylene oxide (PO), ethylene oxide (EO), or a mixture of both oxides. Polymeramines include monoamines, diamines, and triamines based on the core polymer backbone structure. Monoamines are useful because their nucleophilic character, which allows for grafting to a polymer backbone. The broad range of molecular weights, amine functionality, repeating unit type and distribution offers great scope to design new compounds or mixtures.

Both maleic anhydride-grafted polyolefins and polymeramines are commercially available products.

Suitable polymeramines include commercially-available hydrophilic monoamine polyetheramines from Huntsman under trade name Jeffamine®, including for example, Jeffamine M-1000 amine and Jeffamine M-2070 amine have been used. Jeffamine M-1000 is a polyether monoamine of approximately 1000 molecular weight. With a PO/EO mole ratio of about 3/19, Jeffamine M-1000 is relatively hydrophilic a white waxy solid at room temperature. Jeffamine M-2070 is another hydrophilic monoamine based on a polyoxyalkylene copolymer backbone, which is a monofunctional, primary amine with an average molecular weight of about 2,000 g/mol. The propylene oxide/ethylene oxide (PO/EO) mole ratio is about 10/31. The polymeramines result from a reaction of a mono-alcohol initiator with EO and/or PO, followed by conversion of the resulting terminal hydroxyl groups to amines.

Synthesis of Functionalized-PP

The amphiphilic polypropylene-based graft copolymers of the present disclosure combine primary amine functionality from polymeramines with the anhydride of a PP-g-MA compound and it gives an opportunity to generate long chain branched polar PP with a relatively well defined molecular structure. In another words, the chemistry involves a graft-onto reaction between a maleic-anhydride-grafted PP and amine group-terminated polymers. Functionalized-PP has an imide linkage that connects the PP backbone and polyoxyalkylene side chain.

Extent of the reaction is controlled by anhydride concentration in PP-g-MA and ratio between PP-g-MA and polymeramines. Backbone molecular weight, graft length and graft density can be calculated. Optimized imidization reaction produces a long chain branched functionalized-PP with a relatively well-defined molecular structure.

The process to make amphiphilic graft copolymers involves grafting polyoxyalkylene onto a polypropylene (PP) backbone using a reaction of primary amine with anhydride polymerization chemistry. The amphiphilic graft copolymers are prepared starting from maleated polypropylene. The amphiphilic character results from incorporation of hydrophilic polyoxyalkylene side-chains, which include poly(ethyleneoxide) (PEO) and poly(propyleneoxide)(PPO).

The imidization reaction for preparing the amphiphilic graft copolymers involves reacting a maleated PP with a polymeramine in a solvent solution. An exemplary synthesis is reacting a maleic-anhydride terminated PP having Mw~14780 g/mol and Mw/Mn=6.6 with Jeffamine M-2070 with 1/1 mole ratio MA/NH$_2$ units in a xylene solution at 125° C. for 48 hours. A secondary amine (ter-amine) may be present to react with the anhydride to form N-substituted maleimide and to promote dehydration-cyclization reaction and facilitated removing produced water together with the organic solvent from the reaction system. Exemplary ter-amines include but are not limited to: trimethylamine, thri-ethylamine, tripropylamine, tributylamine, tripentylamine, trioctylamine, and tribenzylamine.

Solution polymerization may be used for this synthesis, where the starting materials are in a solvent-based solution. Melt processing may also be used, which may include a twin screw extruder above melting temperature of PP. The term "melt processing" is used to mean any process in which polymers, such as the polyolefin, are melted or softened. Melt processing includes extrusion, pelletization, film blowing or casting, thermoforming, compounding in polymer melt form, fiber spinning, or other melt processes.

Any equipment suitable for a melt processing can be used as long as it provides sufficient mixing and temperature control. For instance, a continuous polymer processing system such as an extruder, a static polymer mixing device such as a Brabender blender, or a semi-continuous polymer processing system, such as a BANBURY mixer, can be used. The term "extruder" includes any machine for polyolefin and TPE extrusion. For instance, the term includes machines that can extrude material in the form of powder or pellets, sheets, fibers, or other desired shapes and/or profiles. Generally, an extruder operates by feeding material through the feed throat (an opening near the rear of the barrel) which comes into contact with one or more screws. The rotating screw(s) forces the polyolefin forward into one or more heated barrels (e.g., there may be one screw per barrel). In many processes, a heating profile can be set for the barrel in which three or more independent proportional-integral-derivative controller (PID)-controlled heater zones can gradually increase the temperature of the barrel from the rear (where the plastic enters) to the front. When a melt extrusion is used, the mixing can take place during the melt extrusion step. The heat produced during the extrusion step provides the energy necessary for the mixing between different components. A temperature at or above the melting temperature of the polymer may be maintained for a time sufficient to mix all the components. For instance, the mixing time may be at least 5 seconds, at least 10 seconds, or at least 15 seconds. Typically, the mixing time is 15-90 seconds.

Suitable blending temperature during melt mixing of polyolefins or TPE with an additive should be sufficient to melt or to soften the component of the composition which has the highest melting or softening point. The temperature typically ranges from 60 to 300° C., for instance, from 100 to 280° C., from 90 to 150° C. One skilled in the art understands that a polyolefin or TPE mixtures thereof typically melts or softens over a temperature range rather than sharply at one temperature. Thus, it may be sufficient that the polyolefin be in a partially molten state. The melting or softening temperature ranges can be approximated from the differential scanning calorimeter (DSC) curve of the polyolefin or mixtures thereof.

An exemplary amphiphilic graft copolymer is shown according to Formula (I).

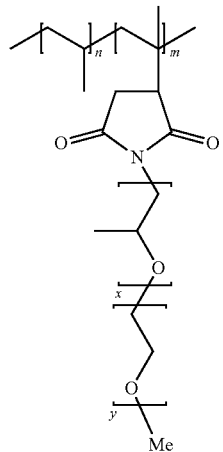

Formula (I)

where Me refers to a methyl ($CH_3$) group. The molar value of m is in the range from 5 to 25 mole percent; and the molar value of n is in the range from 75 to 95 mole percent; the molar value of x is in the range from >0 to 40 propylene oxide units; and the molar value of y is in the range from >0 to 80 ethylene oxide units. Reference to "n" is with respect to the propylene units, "m" is to grafted imide-linked polyoxyalkylene units, "x" is to propylene oxide units of the grafted chain, and "y" is to ethylene oxide units of the grafted chain.

In one or more embodiments, the amphiphilic graft copolymer has a weight average molecular weight (Mw) of about 5,000 to about 300,000 g/mol.

In one or more embodiments, the amphiphilic graft copolymer has a graft density in the range of 0.92 to 1.2 $g/cm^3$.

In one or more embodiments, the graft is hydrophilic. In a detailed embodiment, a molar ratio of EO:PO in the graft is 2:1 or greater.

In one or more embodiments, the amphiphilic graft copolymer has a dispersity index in the range of 1.5 to 9, or 2.5 to 8.

In one or more embodiments, polymerization is performed at a reaction temperature in the range of 120° C. to 240° C. In a specific embodiment, the polymerization is performed at a reaction temperature of greater than 110° C.

In one or more embodiments, the polymerization is performed by solution polymerization. In one or more embodiments, the polymerization is performed by melt processing.

Applications

The amphiphilic graft copolymers in the form of functionalized-PP materials may advantageously be used as modifier in a base polymer formulation, e.g., TPE or polyolefins. The modified base polymer formulations have improved properties with respect to, for example, blending, bonding, paintability, dyeability, printability. The amphiphilic graft copolymers may be co-blended with base formulations to enhance properties of medical devices that are formed by injection molding or by extrusion.

The amphiphilic graft copolymers may be effectively used as a blend compatibilizer in polymer-based systems; especially in those systems where polar fillers, additives, and fibers are used in combination with hydrophobic polymers.

The amphiphilic graft copolymers may be effective to enhance solvent bonding between nonpolar materials, e.g., olefins and/or olefin-based elastomers, and polar polymers such as poly(methyl methacrylate) (PMMA), styrene maleic anhydride (SMA), polycarbonate (PC), and methyl methacrylate-acrylonitrile-butadiene-styrene (MABS). Solvent bonding is a technique used for joining molded plastic parts of medical devices. During the bonding process, the solvent dissolves the surface of two mating parts and allows the material to flow together. Once the solvent evaporates, the result is a material-to-material bond. Many parts of medical devices made from plastics can be solvent-bonded in an application where ultrasonic bonding does not work. For dissimilar materials, however, solvent bonding does not typically achieve a satisfactory bonding. Namely, due to hydrophobicity and low surface energy, the polyolefins and thermoplastic elastomers (TPEs) demonstrate poor interaction and solvent bonding with connector materials that are typically made from the previously-mentioned polar polymers.

By enhancing solvent bonding, it is thought that solvents that are not flammable or carcinogenic may be used, and less harsh bonding techniques that would not impart mechanical stress to medical device components may be used. For example, intravenous tubing sets, which deliver fluids to a patient, need a tubing material that can be securely bonded or welded to connectors which are capable of connection to other parts of the injection device, such as the fluid reservoir, the pump, the pressure pillow, and other tubing. As used herein the term "connector" is understood to include any structure that is part of an intravenous device that is capable of making a connection with a secondary intravenous device. Non-limiting examples of connectors in accordance with the present invention include needleless connectors, male Luer connectors, female Luer connectors, side port valves, y-port valves, port valves, and other similar structures. The term "Luer connectors" includes both luer slip fittings and luer lock fittings. Connectors are preferably formed from polar materials, which are those materials whose polymers have electrons that are not symmetrically distributed resulting in polymers having slightly positive sections and slightly negative sections (e.g., PMMA or SMA or PC or MABS). For the connection of the tubing to the connectors, solvent bonding or welding is a preferred technique because of ease operation, strength and durability of the bond or weld. Also it is a relatively inexpensive process which survives later treatment of the medical products, such as sterilization. Because most of the components of the injection device or set are designed to be single use for medical reasons and therefore must be conveniently disposable, manufacturing cost of the tubing, connectors and other single-use items is particularly important. Typical solvents that have been used for PVC tubing are cyclohexanone or its mixture with methyl ethyl ketone. Therefore, a need exists in the art for a compound that can be used as a modifier for non-polar polyolefin elastomers, which is non-halogenated and also solvent-bondable to the connectors made from the polar polymers. It has to be noted that the compound needed for medical tubing requires extrudability, solvent bondability to the connectors, resistance to kinking, no odor, gamma radiation stability, chemical resistance to drugs flowing through the tubing, low extractables from the tubing, low leachables from the tubing, and non-tackiness after sterilization. For transfer of medicine fluid, clarity of the tube is also strongly preferred for monitoring the flow of the critical medicinal fluid. The present invention solves some of these problems and results in polar PP materials which can be used as a polyolefin elastomer modifier for medical tubing, specifically for the purpose of solvent bonding or welding to connectors for use with other medical equipment.

Further, inclusion of amphiphilic graft copolymers in base polymer formulations can improve paintability, dyeability, printability of various non-polar surfaces, including polyolefin or thermoplastic elastomer (TPE) materials. For example, surfaces of medical devices may directly receive printing ink, which eliminates a need to prepare the surfaces for receipt of labels with adhesives or using other types of surface treatment techniques such as corona/plasma treatment to improve surface energy of the non-polar polymer surfaces.

For injection molded applications the amphiphilic graft copolymers could be used as medical device components such as syringe stoppers, blood collection and closed-system device membranes, and IV drip chambers. As well as for extrusion applications such as IV tubing, catheter extension set tubing and catheter tubing. For all of these applications there is a drive to further enhance, and differentiate, the performance attributes of these devices and components. There is an additional desire from GPOs, NGOs, and regulatory to remove DEHP and other phthalate-based plasticizers from the formulation as well as to eliminate the use of PVC entirely.

Many TPE formulations use some type of plasticizer in their formulation and most IV tubing and extension sets are comprised of plasticized PVC. Additionally, for the stopper application there is a desire to move from the conventional thermal-set rubbers to an injection moldable thermoplastic elastomer which can also be reprocessed, resulting in processing efficiencies and potential cost savings.

For IV tubing TPE formulations cannot yet meet the desired performance attributes of plasticized PVC. Plasticized PVC is desired for its low set, high kink resistance, deformation recoverability, clarity, and tactile feel. An additional challenge with non-polar TPEs is the bonding of the IV tubing to connectors and other fixtures. These connections are typically done via solvent bonding.

For catheter tubing, some materials loose up to 20% of its strength in regions of elevated temperature and humidity, and causes difficulty in catheter stick, threading, advancing, and other catheter related complications.

The present disclosure can be used to address these problems, resulting in a thermoplastic elastomer compound which can be used as medical tubing specifically for the purpose of solvent bonding or welding to connectors for use with other medical equipment.

Some other applications are foam applications for medical components that include closed-cell medical foams for medical device packaging, orthopedic soft goods, and medical components. There is always a need for solutions offering cost performance, mainly by way of weight reduction as well as for ecological friendliness such as recyclability.

Polypropylene (PP) foam offers performance and environmental advantages over polystyrene (PS) foams or other crosslinked foam materials; for example major disadvantage of polyurethane based products is a hydroscopic tendency (water absorption characteristics). Packaging materials made from polyurethane absorb water and gradually disintegrate and lose their quality; PP foam is a durable, lightweight material that offers high resistance to chemicals and moisture. It can be used for the packaging of fragile goods due to its excellent vibration dampening and insulation properties; overall PP foam property and application benefits include: weight reduction, high service and application temperatures, high stiffness, chemical resistance, low-temperature resistance, heat stability for microwavable packaging, good thermal and sound insulation properties, "Soft" touch/paper-like touch, excellent recyclability and ecological friendliness, especially in comparison to conventional alternatives (PS, polyurethane and etc.).

The creation of foamable PP grades has been one of most difficult challenges. Conventional PP inherently exhibits low melt strength and melt extensibility which results in processing problems such as uncontrolled bubble growth in PP foam.

PP modification technology of the present disclosure shows potential to modify polymer structure significantly in order to enhance both melt strength and melt extensibility and makes it possible to produce extruded PP foams with a broad property profile.

Blends for Medical Devices

A base polymeric formulation is a material from which a medical device may be made. Preferably, the base polymeric formulations utilized in conjunction with the amphiphilic graft copolymers disclosed herein comprise at least a polymer or co-polymer of ethylene or polyethylene. The base formulation may further include other ingredients, independently selected from one or more of the following: reinforcing and non-reinforcing fillers, plasticizers, antioxidants, stabilizers, processing oil, extender oils, lubricants, anti-blocking, antistatic agents, waxes, foaming agents, pigments, flame retardants and other processing aids known in the compounding art. Fillers and extenders which can be utilized include conventional inorganics such as calcium carbonate, clays, silica, talc, titanium dioxide, carbon black, and the like. The processing oils generally are paraffinic, naphthenic or aromatic oils derived from petroleum fractions. The oils are selected from those ordinarily used in conjunction with the specific plastics or rubbers present in the formulation.

An additive is a component added to a formulation which is not reactive within the formulation.

Base polymeric materials with PPMA-g-PEO-PPO additive prepared with according to the process of the invention may be formed into useful articles by standard forming methods known in the art, e.g., by blown film extrusion, cast film extrusion, injection or blow molding, pelletizing, foaming, thermoforming, compounding in polymer melt form, or fiber spinning. For example, any technique discussed above in the embodiments describing the melt processes can be used to prepare modified polymer, thereby forming various useful articles, depending on the type of melt processing technique used. For instance, blend may be used in making films, such as blown or cast films. The techniques of blown film extrusion and cast film are known to one skilled in the art in the area of production of thin plastic films. Polymers with PPMA-g-PEO-PPO additive may also be used in coextruded films. The formation of coextruded blown films is known to one skilled in the art. The term "coextrusion" refers to the process of extruding two or more materials through a single die with two or more orifices arranged such that the extrudates merged together into a laminar structure, for instance, before chilling or quenching.

TABLE 2

Exemplary Formulations
(with the proviso that the ingredients total 100%).

| Blend Ingredient | A by weight | B by weight | C by weight |
| --- | --- | --- | --- |
| Base Polymeric Formulation | 95-99.99% | 95-99.99% | 95-99.99% |
| Polypropylene | 50-100% | 0-50% | 0-50% |
| Polyethylene | 0-50% | 50-100% | 0-50% |

TABLE 2-continued

Exemplary Formulations
(with the proviso that the ingredients total 100%).

| Blend Ingredient | A by weight | B by weight | C by weight |
| --- | --- | --- | --- |
| Ethylene-containing Thermoplastic elastomer (TPE) | 0-50% | 0-50% | 50-100% |
| Optional further ingredients | 0-10% | 0-10% | 0-10% |
| PPMA-g-PEO-PPO additive | 0.01-5% | 0.01-5% | 0.01-5% |

In one or more embodiments, including Exemplary Formulations A, B, and C, the PPMA-g-PEO-PPO additive may be present in amounts of about 0.01 to about 5.0% by weight; about 0.1 to about 4.0% by weight; about 0.2 to about 2.0% by weight; about 0.25 to about 0.75% by weight; or about 0.5 weight %.

Polypropylene may be any commercially-available material produced by Ziegler-Natta, Metallocene, or any other olefin polymerization catalyst. Propylene polymers may be homopolymers or copolymers (random or impact). In applications where polypropylene (PP) and polyethylene blends are used, random and impact PP copolymers are preferred; improved compatibility of propylene and ethylene polymers comes from C2 content in the random PP grades. Higher compatibility results in improved physical and mechanical properties for the resulting articles (such as improved tear, dart impact, or puncture resistance in films) as compared with the homopolymer PP resin. The propylene polymers are preferably isotactic or syndiotactic, more preferably isotactic. The preferably melt flow rate of the propylene polymers is in the 0.5-150 g/10 minutes range based on the requirements of the manufacturing process and end-use applications (230° C./2.16 kg, ASTM D1238-13).

Suitable linear low density polyethylene (LLDPE) for use in the process of the invention include copolymers of ethylene and α-olefins. Alpha-olefins include 1-butene, 1-hexene, and 1-octene, the like, and mixtures thereof. The density of LLDPE is preferably within the range of about 0.865 to about 0.925 g/cm$^3$ (ASTM D792-13) and a melt mass flow rate of less than 0.5 g/10 min to greater than 20 g/10 min based on the requirements of the manufacturing process and end application (190° C./2.16 kg, ASTM D1238-13). LLDPE is commercially available, for instance Dowlex™ 2045.01 G LLDPE from Dow Chemical Company. Suitable LLDPE can be produced by a Ziegler-Natta, single-site, or any other olefin polymerization catalysts.

Suitable polyethylene-polypropylene co-polymers may include—reactor grade or melt blended mixtures of the polypropylene and polyethylene polyolefins with or without polyolefin elastomers (final formulation containing from but not limited to about 10 wt.-% up to about 80 wt.-% ethylene and/or propylene monomeric units). The term "blend" or "polymer blend" generally refers to a mixture of two or more components. Such a blend may or may not be miscible, and may or may not be phase separated.

Suitable polyolefins include those prepared from linear or branched olefins having 2 to 20 carbon atoms, 2 to 16 carbon atoms, or 2 to 12 carbon atoms. Typically, the olefin used to prepare the polyolefin is α-olefin. Exemplary linear or branched α-olefins includes, but are not limited to, ethylene, propylene, 1-butene, 2-butene, 1-pentene, 3-methyl-1-butene, 4-methyl-1-pentene, 3-methyl-1-pentene, 1-hexene, 3,5,5-trimethyl-1-hexene, 4,6-dimethyl-1-heptene, 1-octene, 1-decene, 1-undecene, 1-dodecene, 1-tetradecene, 1-hexadecene, 1-octadecene, and 1-eicocene. These olefins may contain one or more heteroatoms such as an oxygen, nitrogen, or silicon. The term "polyolefin" generally embraces a homopolymer prepared from a single type of olefin monomer as well as a copolymer prepared from two or more olefin monomers. A specific polyolefin referred to herein shall mean polymers comprising greater than 50% by weight of units derived from that specific olefin monomer, including homopolymers of that specific olefin or copolymers containing units derived from that specific olefin monomer and one or more other types of olefin comonomers. The polyolefin used herein can be a copolymer wherein the comonomer(s) is/are randomly distributed along the polymer chain, a periodic copolymer, an alternating copolymer, or a block copolymer comprising two or more homopolymer blocks linked by covalent bonds. Typical polyolefins include polyethylene, polypropylene, a copolymer of polyethylene and polypropylene, and a polymer blend containing polyethylene, polypropylene, and/or a copolymer of polyethylene and polypropylene. Polyolefin can also be an ethylene rich impact copolymer (may contain ethylene comonomer at the amount of at least 10 wt.-%; and up to 40 wt.-%), i.e., a heterophasic polyolefin copolymer where one polyolefin is the continuous phase and an elastomeric phase is uniformly dispersed therein. This would include, for instance, a heterophasic polypropylene copolymer where polypropylene is the continuous phase and an elastomeric phase is uniformly dispersed therein. The impact copolymer results from an in-reactor process rather than physical blending. The polyolefins mentioned above can be made by conventional Ziegler/Natta catalyst-systems or by single-site catalyst-systems.

Suitable polyolefin elastomers for use in the process of the invention include ethylene-propylene rubber (EPR), ethylene-propylene-diene monomer rubber (EPDM), the like, and mixtures thereof. As used herein, the term "elastomer" refers to products having rubber-like properties and little or no crystallinity. Preferably, the polyolefin elastomers contain from about 10 wt.-% up to about 80 wt.-% ethylene monomeric units. Illustrative polyolefin elastomers which are commercially available include Lanxess Corporation's BUNA EP T 2070 (22 Mooney ML(1+4) 125° C., 68% ethylene, and 32% propylene); BUNA EP T 2370 (16 Mooney, 3% ethylidene norbornene, 72% ethylene, and 25% propylene); BUNA EP T 2460 (21 Mooney, 4% ethylidene norbornene, 62% ethylene, and 34% propylene); ExxonMobil Chemical's VISTALON 707 (72% ethylene, 28% propylene, and 22.5 Mooney); VISTALON 722 (72% ethylene, 28% propylene, and 16 Mooney); and VISTALON 828 (60% ethylene, 40% propylene, and 51 Mooney). Suitable EP elastomers available from commercial sources also include ExxonMobil Chemical's VISTAMAXX series of elastomers, particularly VISTAMAXX grades 6100, 1100, and 3000. These materials are ethylene-propylene elastomers of 16, 15, and 11 wt.-% ethylene content, respectively, and a Tg of about −20 to −30° C. VISTAMAXX 6100, 1100, and 3000, respectively, have a melt flow rate of 3, 4, and 7 g/10 min at 230° C.; a density of 0.858, 0.862, and 0.871 g/cm$^3$; and a 200 g Vicat softening point of 48, 47, and 64° C. Other suitable elastomers include Dow Chemical's VERSIFY propylene-ethylene copolymers, particularly grades DP3200.01, DP3300.01, and DP3400.01, which have nominal ethylene contents of 9, 12 and 15 wt.-%, respectively, and corresponding nominal propylene contents of 91, 88, and 85 wt.-%, respectively. These grades have a melt flow rate of 8 g/10 min at 230° C.; a density of 0.876, 0.866, and 0.858 g/cm$^3$, respectively; a Vicat softening point of 60, 29, and <20° C., respectively; and a Tg of −25, −28, and −31° C., respectively.

Preferably, the polyolefin elastomers contain from but not limited to about 10 wt.-% up to about 80 wt.-% ethylene monomeric units. The term "thermoplastic elastomer" (TPE) in general defines blends of polyolefins and rubbers in which blends of the rubber phase is not cured, i.e., so called thermoplastic olefins (TPO), blends of polyolefins and rubbers in which blends of the rubber phase has been partially or fully cured by a vulcanization process to form thermoplastic vulcanizates (TPV), or unvulcanized block-copolymers or blends thereof. Non-polar thermoplastic elastomer may made from a thermoplastic polyolefin homopolymer or copolymer, and an olefinic rubber which is fully crosslinked, partially crosslinked or not crosslinked, and optionally commonly used additives; as well as a block-copolymer of styrene/conjugated diene/styrene and/or its fully or partially hydrogenated derivative.

Polyolefins suitable for use in TPE composition include thermoplastic, semi-crystalline polyolefin homopolymers and copolymers. They are desirably prepared from monoolefin monomers having but not limited to 2 to 7 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. The polyolefins which can be used in TPE formulations can be a high, low, linear-low, very low-density polyethylenes and copolymers of ethylene with (meth)acrylates and/or vinyl acetates. Polyolefins can be made by conventional Ziegler/Natta catalyst-systems or by single-site catalyst-systems, or other polyolefin catalyst technology in combination with various process technologies and solutions.

Suitable olefinic rubbers of the monoolefin copolymer rubbers comprise non-polar, rubbery copolymers of two or more α-monoolefins, preferably copolymerized with at least one polyene, usually a diene. Saturated monoolefin copolymer rubber, for example ethylene-propylene copolymer rubber (EPM) can be used. However, unsaturated monoolefin rubber such as EPDM rubber is more suitable. EPDM is a terpolymer of ethylene, propylene and a non-conjugated diene. Satisfactory non-conjugated dienes include 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; dicyclopentadiene (DCPD) and vinyl norbornene (VNB). Butyl rubbers are also used in TPE formulation. The term "butyl rubber" includes copolymers of an isoolefin and a conjugated monoolefin, terpolymers of an isoolefin with or without a conjugated monoolefin, divinyl aromatic monomers and the halogenated derivatives of such copolymers and terpolymers. Another suitable copolymer within the olefinic rubber is a copolymer of a $C_{4-7}$ isomonoolefin, and a para-alkylstyrene. A further olefinic rubber used in TPE is natural rubber. The main constituent of natural rubber is the linear polymer cis-1,4-polyisoprene. Furthermore polybutadiene rubber and styrene-butadiene-copolymer rubbers can also be used. Blends of any of the above olefinic rubbers can be employed, rather than a single olefinic rubber. Further suitable rubbers are nitrite rubbers. Examples of the nitrile group-containing rubber include a copolymer rubber comprising an ethylenically unsaturated nitrile compound and a conjugated diene. Further, the copolymer rubber may be one in which the conjugated diene units of the copolymer rubber are hydrogenated. Specific examples of the ethylenically unsaturated nitrile compound include acrylonitrile, α-chloroacrylonitrile, α-fluoroacrylonitrile and methacrylonitrile. Among them, acrylonitrile is particularly preferable. Other suitable rubbers are based on polychlorinated butadienes such as polychloroprene rubber. These rubbers are commercially available under the trade names Neoprene® and Bayprene®.

A commercially available thermoplastic elastomer (TPE) for use herein may be one formulated without plasticizers having a nominal density of 0.888 g/cm³ (ASTM D792-13) and a nominal composition of: 33.0 mol % propylene, 24.8 mol % ethylene, and 42.2 mol % butylene.

Turning to FIG. 2, a portion of an intravenous (IV) infusion kit comprising tubing, an IV injection port, and connection is illustrated. A patient is connected to an IV source by means of an intravenous (IV) infusion kit. The kit comprises a length of tubing having connectors on the ends and one or more injection sites or ports. The injection sites or ports enable the injection of additional medications or the like via a syringe or other IV source. The exemplary kit, as illustrated, comprises a needle 12 for insertion into a patient connected to tubing 14 having a Y-site (connector) 16, and a tubing branch 18 for connection to a source of IV fluid (not shown). The Y-site includes a conventional IV injection site or port comprising an elastic plug and cap combination 20 of Neoprene or the like on or over the end of a portion of the Y-tube. The connection of an additional IV source for the injection of a fluid is accomplished by inserting a conventional needle 22 through the site or port 20 into the underlying tube. Embodiments of the present invention include tubing 14 being formed from a base polymeric formulation comprising a polyolefin (e.g., polyethylene or polypropylene) or a thermoplastic elastomer (TPE) to which is added an additive comprising a functionalized-PP material. The Y-site (connector) 16 may be formed from a material selected from the group consisting of: poly(methyl methacrylate) (PMMA), styrene maleic anhydride (SMA), polycarbonate (PC), and methyl methacrylate-acrylonitrile-butadiene-styrene (MABS). The tubing 14 is solvent-bonded to the Y-site (connector) 16.

EMBODIMENTS

Various embodiments are listed below. It will be understood that the embodiments listed below may be combined with all aspects and other embodiments in accordance with the scope of the invention.

Embodiment 1

An amphiphilic copolymer of Formula (I):

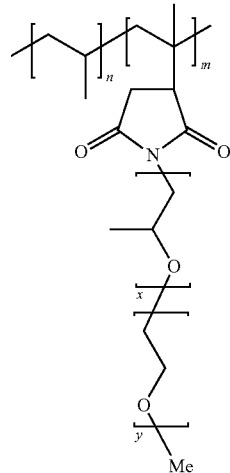

Formula (I)

wherein Me is $CH_3$; the molar value of m is in the range from 5 to 25 mole percent; and the molar value of n is in the range from 75 to 95 mole percent; the molar value of x is in the range from >0 to 40 propylene oxide units; and the molar value of y is in the range from >0 to 80 ethylene oxide units.

Embodiment 2

The amphiphilic copolymer of embodiment 1 having a weight average molecular weight (Mw) in the range of about 5,000 to about 300,000 g/mol.

Embodiment 3

The amphiphilic copolymer of one of embodiments 1 to 2 having a molar ratio of EO:PO of 2:1 or greater.

Embodiment 4

The amphiphilic copolymer of one of embodiments 1 to 3 having a dispersity index in the range of 1.5 to 9.

Embodiment 5

A process for preparing an amphiphilic copolymer comprising: obtaining a maleated polypropylene; and polymerizing the maleated polypropylene with a polymeramine having monoamine functionality to form the amphiphilic copolymer; wherein the amphiphilic copolymer comprises a polypropylene backbone and polyoxyalkylene side-chains.

Embodiment 6

The process of embodiment 5, wherein the amphiphilic copolymer is according to Formula (I):

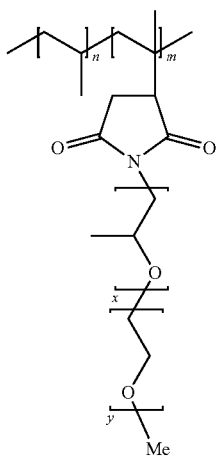

Formula (I)

wherein Me is CH$_3$; the molar value of m is in the range from 5 to 25 mole percent; and the molar value of n is in the range from 75 to 95 mole percent; the molar value of x is in the range from >0 to 40 propylene oxide units; and the molar value of y is in the range from >0 to 80 ethylene oxide units.

Embodiment 7

The process of one of embodiments 5 to 6, wherein the polymerization is performed at a reaction temperature in the range of 120° C. to 240° C.

Embodiment 8

The process of one of embodiments 5 to 7, wherein the polymerization is performed via solution polymerization.

Embodiment 9

The process of one of embodiments 5 to 8, wherein the polymerization is performed via melt processing.

Embodiment 10

A medical device formed from a blend comprising: a base polymeric formulation comprising at least a polymer or co-polymer of propylene; and an additive comprising a polypropylene-poly(ethylene oxide)-poly(propylene oxide) amphiphilic graft copolymer (PPMA-g-PEO-PPO); the PPMA-g-PEO-PPO being present in the blend in an amount in the range of about 0.01 to about 5.0% by weight of the blend.

Embodiment 11

The medical device of embodiment 10, wherein the PPMA-g-PEO-PPO is according to Formula (I):

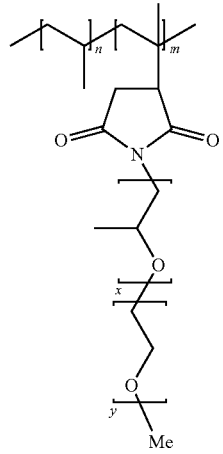

Formula (I)

wherein Me is CH$_3$; the molar value of m is in the range from 5 to 25 mole percent; and the molar value of n is in the range from 75 to 95 mole percent; the molar value of x is in the range from >0 to 40 propylene oxide units; and the molar value of y is in the range from >0 to 80 ethylene oxide units.

Embodiment 12

The medical device of one of embodiments 10 to 11, wherein the base polymeric formulation comprises polypropylene, a polyethylene-polypropylene co-polymer, a polypropylene-containing thermoplastic elastomer (TPE), or combinations thereof.

Embodiment 13

The medical device of one of embodiments 10 to 12, wherein the PPMA-g-PEO-PPO is a product of polymerization of a maleated polypropylene and a polymeramine having monoamine functionality.

Embodiment 14

The medical device of one of embodiments 10 to 13, wherein the PPMA-g-PEO-PPO has a weight average molecular weight (Mw) in the range of about 5,000 to about 300,000 g/mol.

Embodiment 15

The medical device of one of embodiments 10 to 14, wherein the PPMA-g-PEO-PPO has a molar ratio of EO:PO of 2:1 or greater.

Embodiment 16

The medical device of one of embodiments 10 to 15, wherein the PPMA-g-PEO-PPO has a dispersity index in the range of 1.5 to 9.

Embodiment 17

The medical device of one of embodiments 10 to 16 in the form of tubing.

EXAMPLES

Example 1

Synthesis.

10 grams PP-g-MA (Aldrich) (average Mw approximately 9,100 by GPC, average Mn approximately 3,900 by GPC, maleic anhydride 8-10 wt %) and 10 grams Jeffamine M2070 (Huntsman), were suspended in 200 ml Xylene (Fisher), and 2 g Tripropylamine (Sigma-Aldrich), was added afterward. The suspension was heated up to 125° C. for 48 hours. No initiator was used because it is a N-imidation reaction.

Purification.

Graft copolymer solution in xylene was precipitated in acetone (Fisher), rinsed with acetone (Fisher) and solvent extraction with Acetone (Fisher) for 24 hours. Tripropylamine is removed during this step. Purified material was dried in the vacuum oven overnight.

Yield.

PPMA-g-Jeffamine (e.g., PPMA-g-PEO-PPO) was ~85% after purification based on the starting amount of PP-g-MA.

Example 2

Testing

Differential Scanning Calorimetry (DSC).

Two heating steps and one cooling step were performed for each sample under −20 to 200° C. temperature range, using 10° C./min heating rate. Collected DSC thermograms were used to calculate melting, crystallization temperatures and degree of crystallinity.

FIG. 3 is a thermogram of heat flow (mW) for the starting materials and final polymer versus temperature (° C.) for a first range of temperatures during a second heating. Table 1 shows melting points after the second heating step ($T_m$).

TABLE 1

| Sample Name | $T_c$ (° C.) | $T_m$ (° C.) |
|---|---|---|
| PP-MA | N/A | N/A |
| Jeffamine | ND | 3.8 |
| PPMA-g-Jeffamine | ND | 18.6 |

The DSC temperature range below 60° C. is informative of the Jeffamine M-2070 raw material and the impact of the grafting onto PP-g-MA. Jeffamine M-2070 has characteristic melting peak around 3.2-3.8° C. that moves to high temperature side after reaction with PP-g-MA; namely melting temperature of grafted propylene oxide/ethylene oxide (PO/EO) segment from polyetheramine (Jeffamine) is shifted to 18-19° C. DSC did not detect crystallization of Jeffamine before or after grafting.

Figure 4:
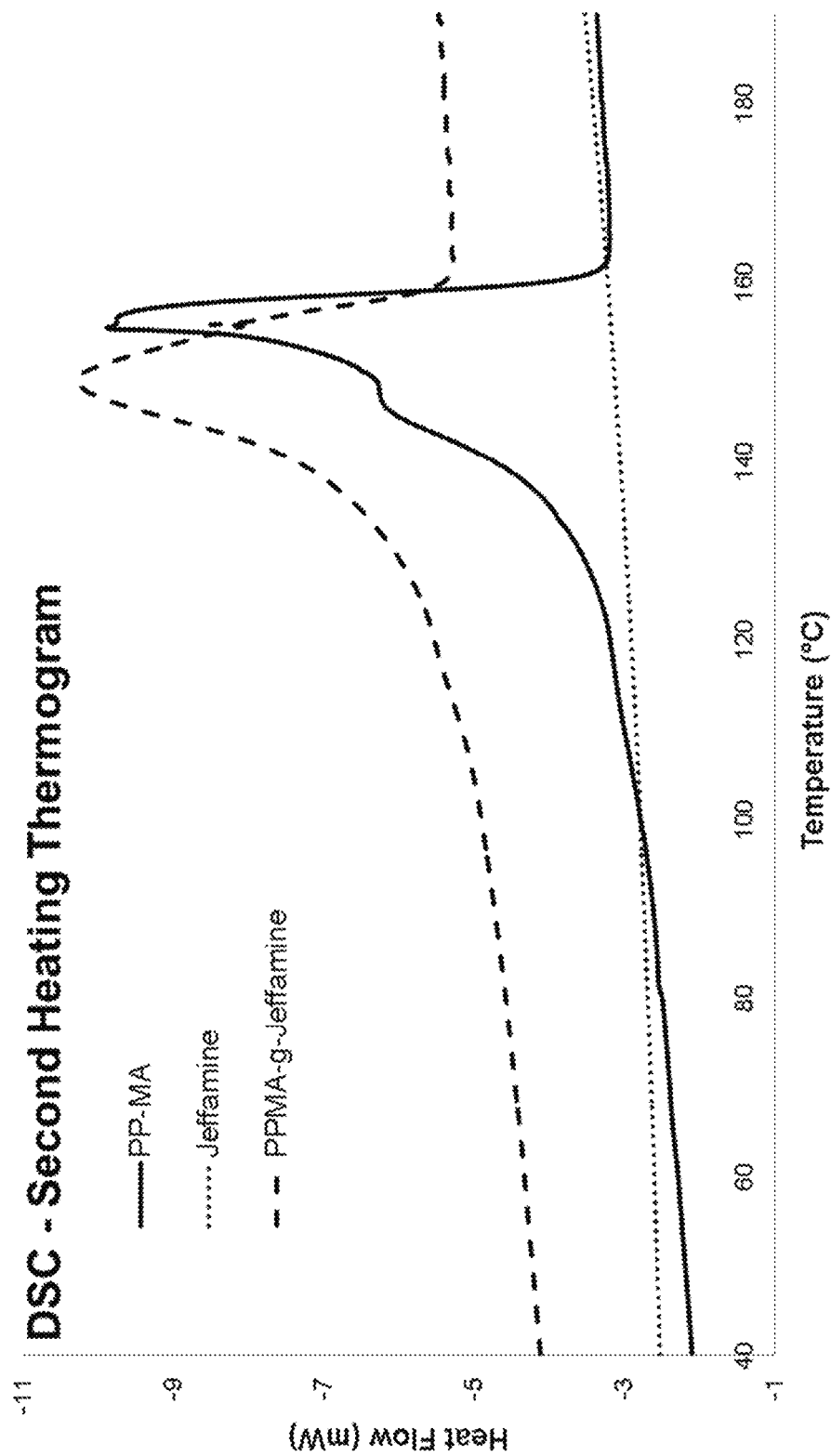
FIG. 4 is a thermogram of heat flow (mW) for the starting materials and final polymer versus temperature (° C.) for a second range of temperatures during a second heating.
Figure 5:
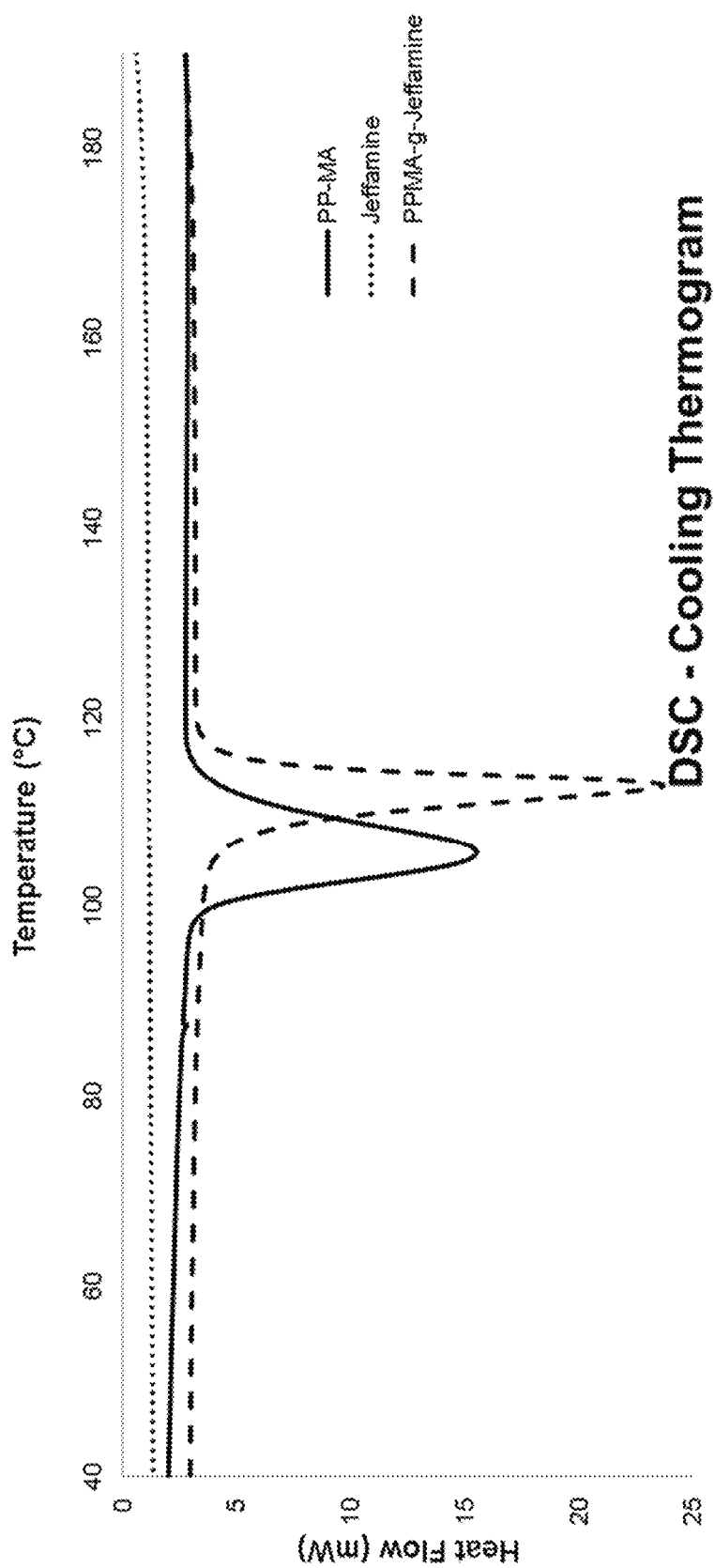
FIG. 5 is a thermogram of heat flow (mW) for the starting materials and final polymer versus temperature (° C.) for a second range of temperatures during a cooling.

FIG. 4 is a thermogram of heat flow (mW) for the starting materials and final polymer versus temperature (° C.) for a second range of temperatures during a second heating. Table 2 shows crystallinity temperature (Tc), $\Delta H_c$, and % crystallinity; and melting point ($T_m$), $\Delta H_m$, and % crystallinity after the second heating step. FIG. 5 is a thermogram of heat flow (mW) for the starting materials and final polymer versus temperature (° C.) for a second range of temperatures during a cooling.

TABLE 2

| Sample Name | $T_c$ (° C.) | $\Delta H_c$ (J/g) | Crystallinity (%) | $T_m$ (° C.) | $\Delta H_m$ (J/g) | Crystallinity (%) |
|---|---|---|---|---|---|---|
| PP-MA | 105.7 | 69.0 | 33.3 | 154.7 | 66.3 | 32.0 |
| Jeffamine | N/A | N/A | N/A | N/A | N/A | N/A |
| PPMA-g-Jeffamine | 112.8 | 71.1 | 34.3 | 148.9 | 68.0 | 32.8 |

The DSC temperature range above 60° C. is informative of the PP-g-MA raw material and the impact of the grafting onto PP-g-MA. DSC results show that incorporation of polar groups depresses slightly (~1-2° C.) melting temperature of polypropylene (PP) and increases slightly crystallization degree of PP (~1% increase) of the grafted PPMA-g-Jeffamine resin; DSC thermograms of PPMA-g-Jeffamine also show that crystallization temperature (Tc) of PP increases by ~7° C. after grafting. Increase of Tc is based on chain length and branching, namely by incorporation propylene oxide/ethylene oxide (PO/EO) segment (chains). Mechanical properties such as ductility, tensile strength, and hardness rise and eventually level off with increasing chain length.

Thermogravimetric Analysis (TGA).

Figure 6:
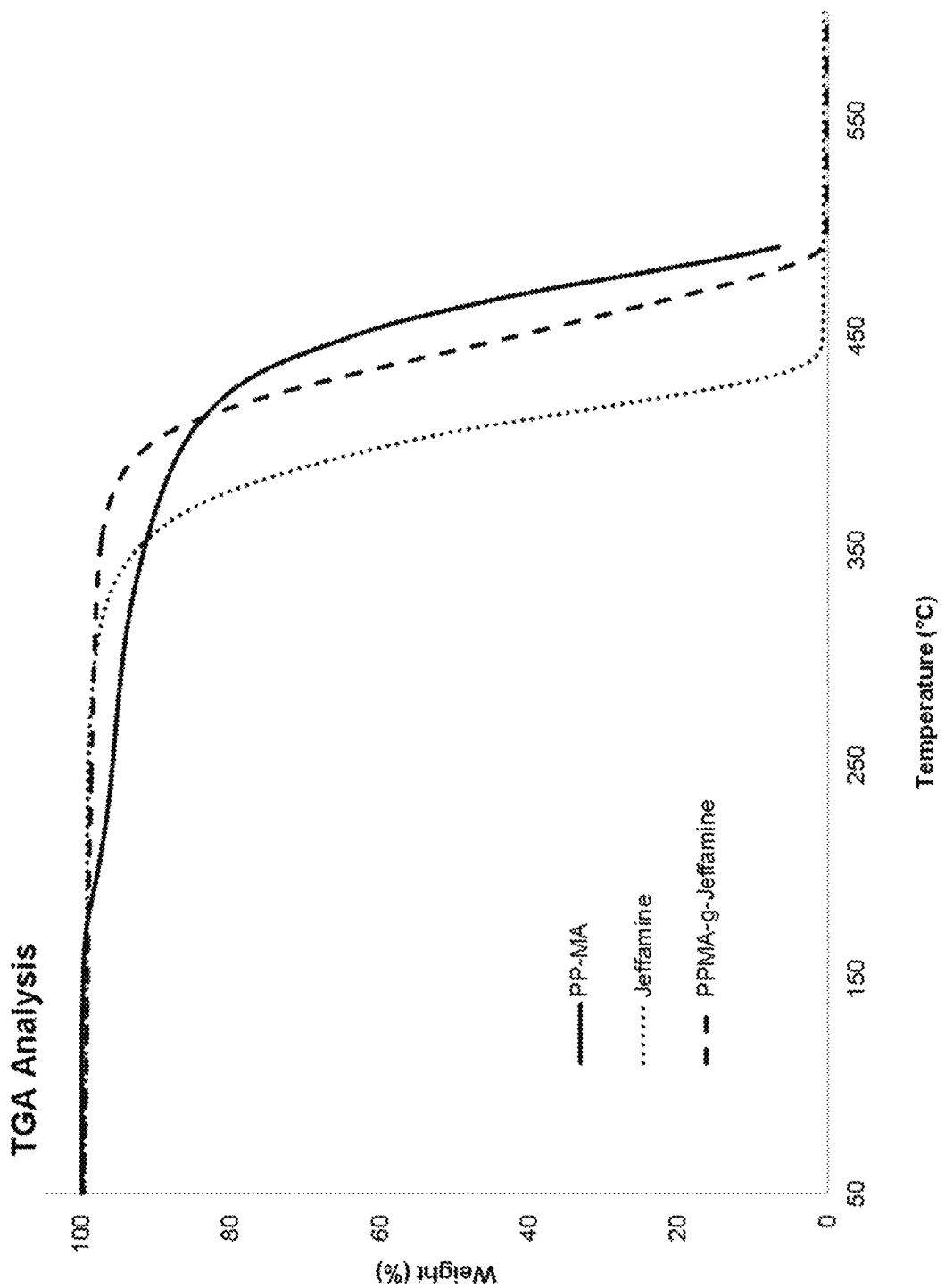
FIG. 6 is a graph of weight % versus temperature by Thermogravimetric Analysis (TGA)

In order to get materials thermal degradation profile (heat resistance behavior), samples were heated from room temperature to 500° C. using 20° C./min heating rate. Table 3 shows residue in weight % after 250° C. or 355° C. FIG. 6 is a graphical depiction of the TGA data.

TABLE 3

| Sample Name | Residue (wt. %) at 250° C. | Residue (wt. %) at 355° C. |
|---|---|---|
| PP-MA | 95.9 | 91.3 |
| Jeffamine | 99.1 | 90.8 |
| PPMA-g-Jeffamine | 98.7 | 97.3 |

TGA scans of PP-g-MA sample shows that PP contains around 8 wt. % of grafted maleic anhydride groups; compare to Jeffamine and PPMA-g-Jeffamine samples, PP-g-MA starts thermal decomposition at lower temperature ~190° C., while Jeffamine and PPMA-g-Jeffamine are showing major decomposition at 300 and 350° C., respectively.

TGA thermograms confirm transformation of the maleic anhydride groups and occurrence of the propylene oxide/ethylene oxide (PO/EO) chain grafting.

Compared to starting polymers, PPMA-g-Jeffamine shows the best thermal stability; at 355° C. temperature it is losing only 2.7 wt. %.

Gel Permeation Chromatography (GPC).

Polymer Lab (PL) GPC 220 high temperature GPC system was used, with TCB solvent (containing 0.0125% BHT stabilizer) at 1 mL/min, using 3 PL gel 10 μm MIXED-B columns and refractive index detector, at 160° C., 200 μL injection volume, and 45 min run time. Samples were dissolved in TCB with heating at approximately 1.5 mg/mL. Molecular weight was based on polystyrene standards, using the following Mark-Houwink parameters:

| Polystyrene in TCB | K = 12.1 × 10−5, α = 0.707 |
|---|---|
| Polypropylene in TCB | K = 19.0 × 10−5, α = 0.725 |

Figure 7:
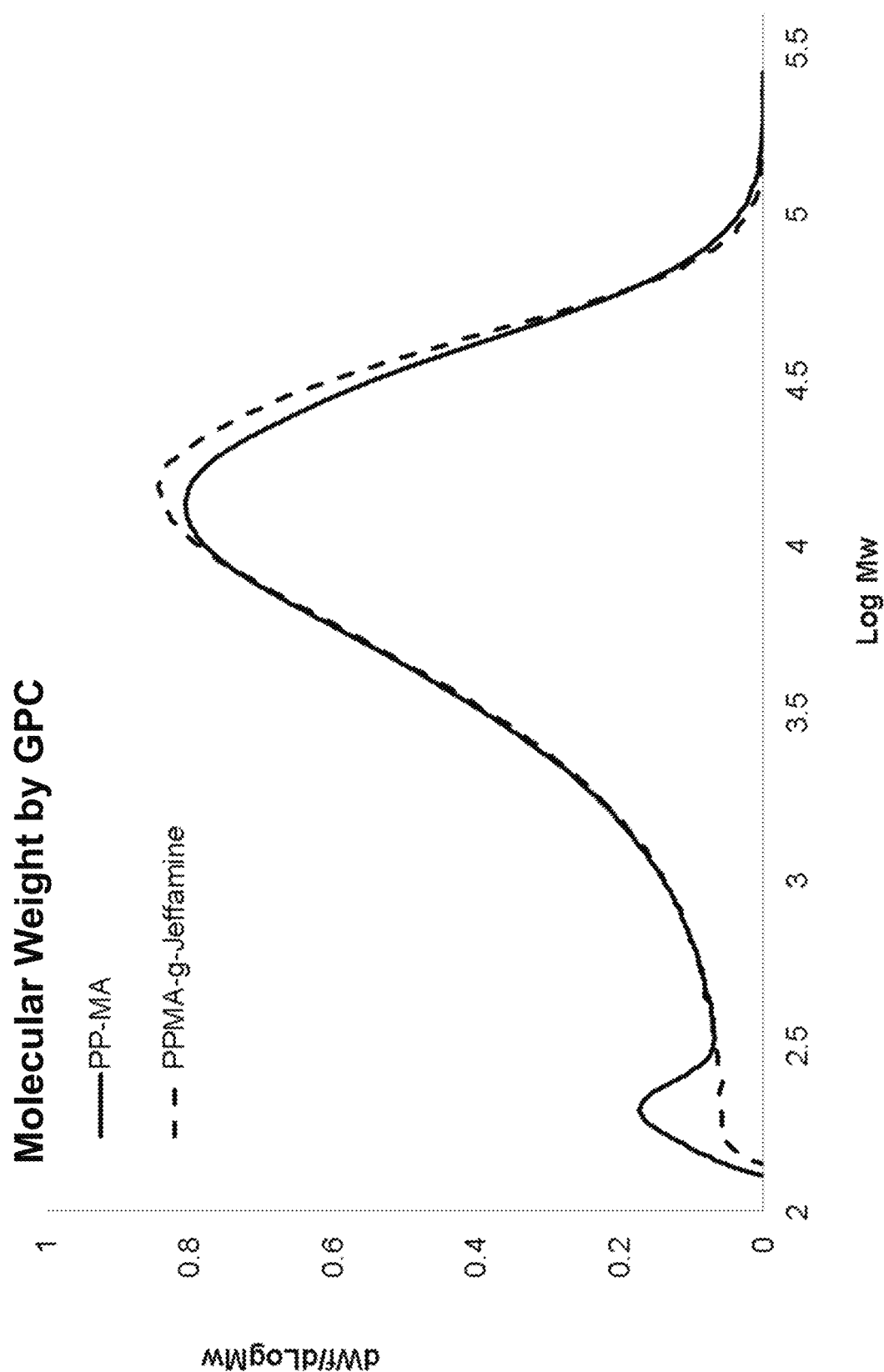
FIG. 7 is a molecular weight graph by gel permeation chromatography.

Table 4 provides molecular weight parameters of the raw materials and amphiphlic graft copolymer, where Mp is _peak average molecular weight, Mn is number-average molecular weight, Mw is weight-average molecular weight, and PD is polydispersity. FIG. 7 provides a molecular weight graph by gel permeation chromatography for the PP-g-MA and the PPMA-g-Jeffamine.

TABLE 4

| Sample Name | Mp | Mn | Mw | PD |
|---|---|---|---|---|
| PP-MA | 13305 | 2226 | 14780 | 6.64 |
| Jeffamine | N/A | 2357 | 2713 | 1.15 |
| PPMA-g-Jeffamine | 14927 | 3135 | 15225 | 4.86 |

GPC curve shows that PP-g-MA contains high amount of low molecular weight fractions; content of low molecular weight is so high in PP-g-MA resin that molecular weight curve shows almost bi-modal distribution. Molecular weight distribution curve changes dramatically after reaction of PP-g-MA with Jeffamine; namely molecular weight distribution of PPMA-g-Jeffamine sample becomes narrow and content of low molecular weight fractions decreases.

GPC data also shows that compare to starting polymers (Jeffamine and PPMA), grafting increases average molecular weight of the obtained resin.

Fourier Transform Infrared Spectroscopy (FTIR).

Figure 8:
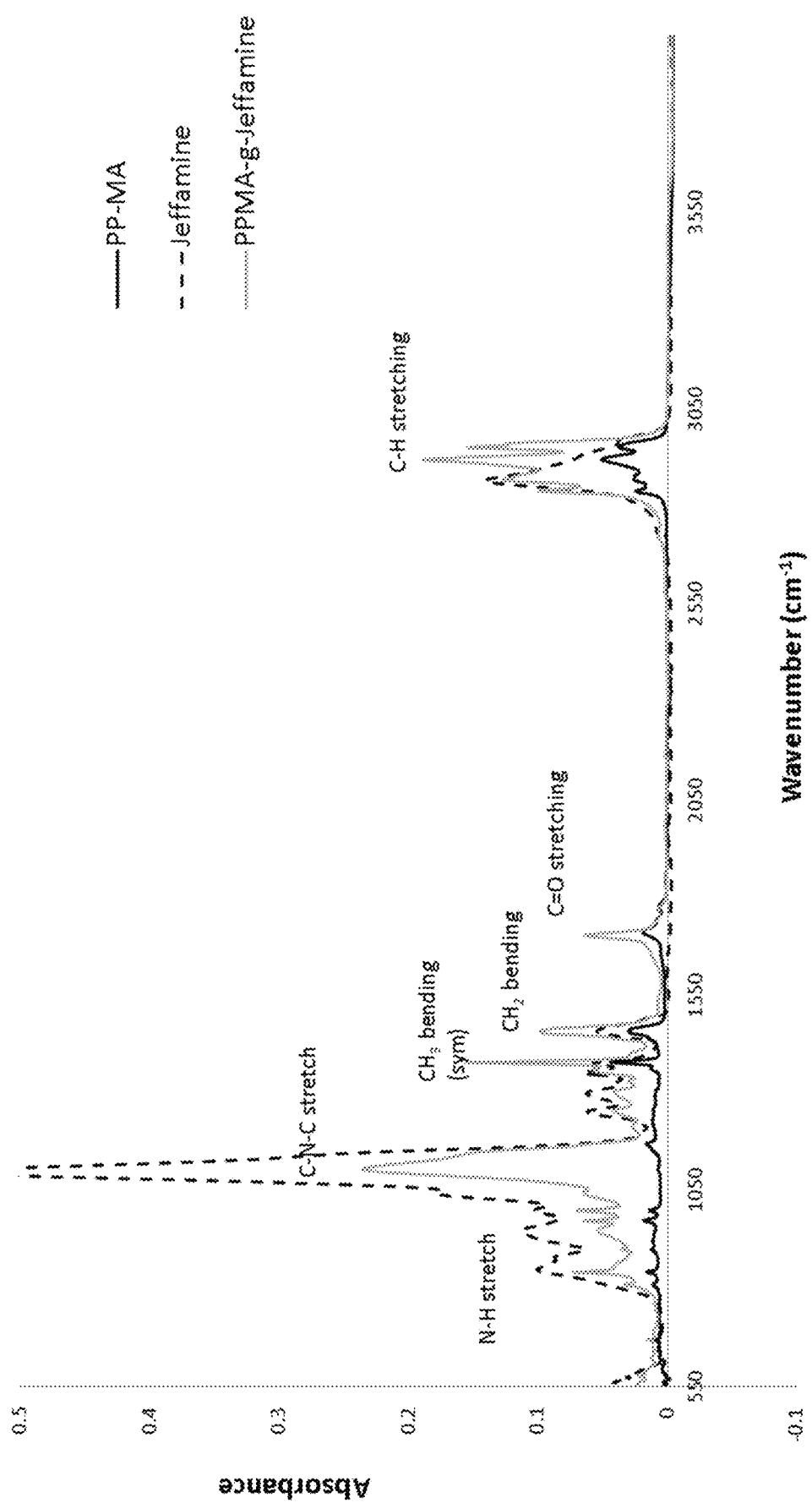
FIG. 8 provides FTIR spectra of the starting materials and final polymer.

FTIR spectra of the starting materials and final polymer were collected in 550-4000 cm$^{-1}$ range using 32 scans. FIG. 8 provides FTIR spectra of the starting materials and final polymer. Formation of the imide groups in the polymer was confirmed by monitoring (1) changes of C—N stretching signals, (2) increase intensity of carbonyl C=O groups bound to nitrogen (in the imide group) and (3) formation characteristic imide ring band. The typical doublet bands of C=O group stretching bands in the imide group are found at 1703-1718 cm$^{-1}$ (asymmetric stretch) and 1783 cm$^{-1}$ (symmetric stretch). Other characteristic peaks of imide group include C—N stretching at 1345 cm$^{-1}$, transfer stretching of C—N—C groups at 1087 cm$^1$ and out-of-plane bending of C—N—C groups at 714 cm$^1$. FTIR spectra of PPMA-g-Jeffamine also shows characteristic imide ring band around 1391-1400 cm$^{-1}$ wavenumber.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device formed from a blend comprising:
a base polymeric formulation comprising at least a polymer or co-polymer of propylene; and
an additive comprising a polypropylene-poly(ethylene oxide)-poly(propylene oxide) amphiphilic graft copolymer (PPMA-g-PEO-PPO);
the PPMA-g-PEO-PPO being present in the blend in an amount in the range of about 0.01 to about 5.0% by weight of the blend;
wherein the PPMA-g-PEO-PPO is according to Formula (I):

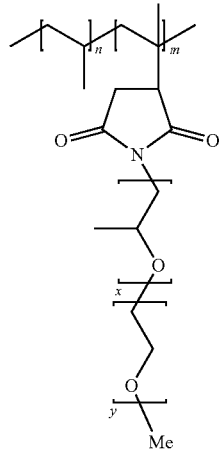

Formula (I)

wherein Me is CH$_3$; the molar value of m is in the range from 5 to 25 mole percent; and
the molar value of n is in the range from 75 to 95 mole percent; the molar value of x is in the range from >0 to 40 propylene oxide units; and the molar value of y is in the range from >0 to 80 ethylene oxide units, and
wherein the medical device is in the form of tubing.

2. The medical device of claim 1, wherein the base polymeric formulation comprises polypropylene, a polyethylene-polypropylene co-polymer, a polypropylene-containing thermoplastic elastomer (TPE), or combinations thereof.

3. The medical device of claim 1, wherein the PPMA-g-PEO-PPO is a product of polymerization of a maleated polypropylene and a polymeramine having monoamine functionality.

4. The medical device of claim 1, wherein the PPMA-g-PEO-PPO has a weight average molecular weight (Mw) in the range of about 5,000 to about 300,000 g/mol.

5. The medical device of claim 1, wherein the PPMA-g-PEO-PPO has a molar ratio of EO:PO of 2:1 or greater.

6. The medical device of claim 1, wherein the PPMA-g-PEO-PPO has a dispersity index in the range of 1.5 to 9.

* * * * *